(12) United States Patent
Konomura

(10) Patent No.: US 8,764,635 B2
(45) Date of Patent: Jul. 1, 2014

(54) ENDOSCOPE APPARATUS

(75) Inventor: Yutaka Konomura, Tokyo (JP)

(73) Assignee: Olympus Corporation, Tokyo (JP)

( * ) Notice: Subject to any disclaimer, the term of this patent is extended or adjusted under 35 U.S.C. 154(b) by 589 days.

(21) Appl. No.: 12/953,646

(22) Filed: Nov. 24, 2010

(65) Prior Publication Data

US 2012/0130168 A1  May 24, 2012

(51) Int. Cl.
*A61B 1/04* (2006.01)
*A61B 1/06* (2006.01)

(52) U.S. Cl.
USPC ............... 600/111; 600/166; 600/181

(58) Field of Classification Search
USPC ................... 600/111, 166, 181, 109
See application file for complete search history.

(56) References Cited

U.S. PATENT DOCUMENTS

| | | | |
|---|---|---|---|
| 6,063,023 A | 5/2000 | Sakiyama et al. | |
| 8,465,415 B2* | 6/2013 | Ogawa | 600/103 |
| 2009/0292166 A1* | 11/2009 | Ito et al. | 600/109 |
| 2010/0201795 A1* | 8/2010 | Sato et al. | 348/65 |
| 2010/0208046 A1* | 8/2010 | Takahashi | 348/65 |

FOREIGN PATENT DOCUMENTS

JP    10-248806 A    9/1998

* cited by examiner

*Primary Examiner* — Anhtuan T Nguyen
*Assistant Examiner* — Alexandra Newton
(74) *Attorney, Agent, or Firm* — Holtz Holtz Goodman & Chick PC

(57) ABSTRACT

An endoscope apparatus is adapted to be inserted into an inside of a subject and observe the inside of the subject and includes: an observation optical system which has a first optical path and a second optical path with parallax; an imaging portion on which a light passing through the first optical path and a light passing through the second optical path are formed; a diaphragm portion which selectively blocks out the first optical path or the second optical path; a distance measurement portion which measures a distance to the subject on the basis of parallax between a first image formed on the imaging portion via the first optical path and a second image formed on the imaging portion via the second optical path; a displacement amount detection portion which detects a displacement amount between two first images acquired with a time interval therebetween; and a measurement environment determination portion which determines, on the basis of the displacement amount, whether or not the first image and the second image are suitably used for measurement by the distance measurement portion.

3 Claims, 9 Drawing Sheets

000000000000

ENDOSCOPE APPARATUS

BACKGROUND OF THE INVENTION

1. Field of the Invention

The present invention relates to an endoscope apparatus, more specifically, to an endoscope apparatus which is capable of performing distance measurement using stereo measurement.

2. Description of Related Art

Conventionally, an endoscope which includes a narrow, elongated insertion portion and an observation device, such as an optical system and an imaging device, which is attached to the distal end of the insertion portion, is used to observe the inside of a subject. Among endoscopes having the above-described structure, there is known an endoscope which is capable of measuring the distance between an observation target inside the subject and the distal end of the insertion portion.

For example, Japanese Unexamined Patent Application, First Publication No. H10-248806 discloses an endoscope apparatus which has an optical adaptor with a pair of objective lenses. This endoscope apparatus performs a three-dimensional measurement (hereinafter referred to as "stereo measurement") with stereo image processing using two right and left image data of a subject to be measured, the image data being acquired via the optical adaptor.

SUMMARY OF THE INVENTION

An endoscope apparatus according to a first aspect of the present invention is adapted to be inserted into an inside of a subject and observe the inside of the subject and includes: an observation optical system which has a first optical path and a second optical path with parallax; an imaging portion on which a light passing through the first optical path and a light passing through the second optical path are formed; a diaphragm portion which selectively blocks out the first optical path or the second optical path; a distance measurement portion which measures a distance to the subject on the basis of parallax between a first image formed on the imaging portion via the first optical path and a second image formed on the imaging portion via the second optical path; a displacement amount detection portion which detects a displacement amount between two first images acquired with a time interval therebetween; and a measurement environment determination portion which determines, on the basis of the displacement amount, whether or not the first image and the second image are suitably used for measurement by the distance measurement portion.

An endoscope apparatus according to a second aspect of the present invention is adapted to be inserted into an inside of a subject and observe the inside of the subject and includes: a distance measurement portion which measures a distance to the subject on the basis of an image of the subject; a displacement amount detection portion which detects, on the basis of images of the subject acquired with a time interval therebetween, a displacement amount between the images; and a measurement environment determination portion which determines, on the basis of the displacement amount, whether or not measurement by the distance measurement portion is suitably performed.

DETAILED DESCRIPTION OF THE INVENTION

Hereinafter, a first embodiment of the present invention will be described with reference made to FIGS. 1 through 9.

Figure 1:
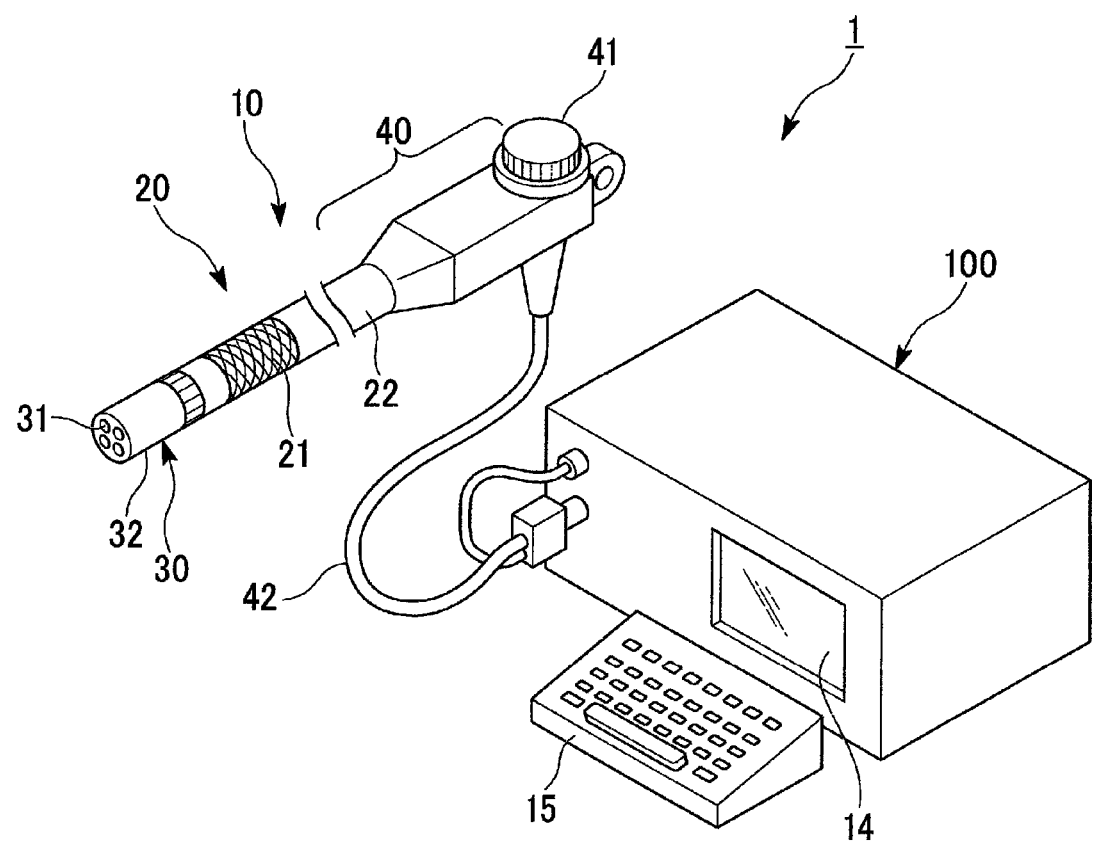
FIG. 1 shows the entire structure of an endoscope apparatus according to a first embodiment of the present invention.

FIG. 1 shows the entire structure of an endoscope apparatus 1 of the first embodiment. The endoscope apparatus 1 is used to observe an inside of a subject, and includes: an endoscope 10 which acquires an image of the subject; and a processing device 100 which performs various processing such as measurement on the basis of the image acquired by the endoscope 10.

The endoscope 10 includes: a narrow, elongated insertion portion 20 which is inserted into the inside of the subject; an optical adaptor 30 which is attached to the distal end of the insertion portion 20; and an operation portion 40 which is used to operate the insertion portion 20.

The insertion portion 20 includes: a bent portion 21 with a known structure formed of a plurality of joint rings or bent pieces; and a flexible tube portion 22 which connects the bent portion 21 and the operation portion 40. The bent portion 21 is capable of being bent in a desired direction by the operation of the operation portion 40. An imaging device 23 (described later) such as a CCD, on which an image of the subject is formed via the optical adaptor 30, is arranged at the distal end of the insertion portion 20 so that the imaging device 23 can be freely attached to or detached from the insertion portion 20.

Figure 2:
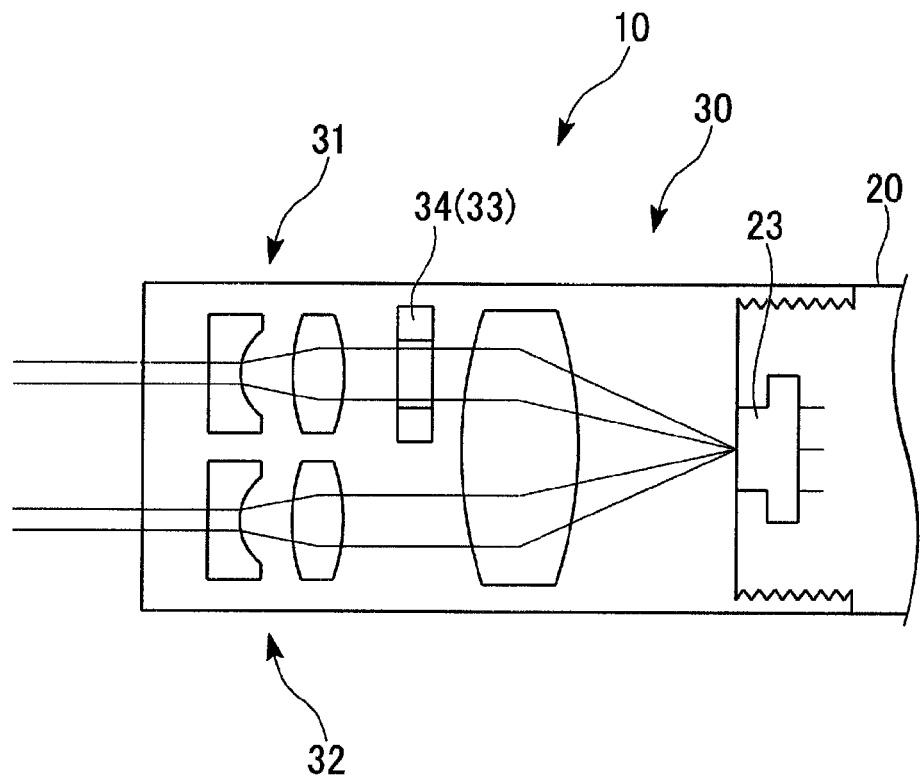
FIG. 2 is a pattern diagram showing a distal end of an insertion portion and an optical adaptor of an endoscope in the same endoscope apparatus.

FIG. 2 is a pattern diagram showing the distal end of the insertion portion 20 and the optical adaptor 30. As shown in FIGS. 1 and 2, the optical adaptor 30 includes: two objective optical systems of a first objective optical system 31 and a second objective optical system 32 which are arranged in parallel and used to observe the subject; and a diaphragm portion 33 which selectively blocks out an optical path (referred to as first optical path) of the first objective optical system 31 or an optical path (referred to as second optical path) of the second objective optical system 32. The beam of light passing through the first optical path and the beam of light passing through the second optical path are formed on the imaging device (i.e., imaging portion) 23, thereby acquiring an image of the subject. Since there is a parallax between the first optical path and the second optical path, a certain amount of parallax also exists between the image acquired via the first optical path and the image acquired via the second optical path.

Figure 3:
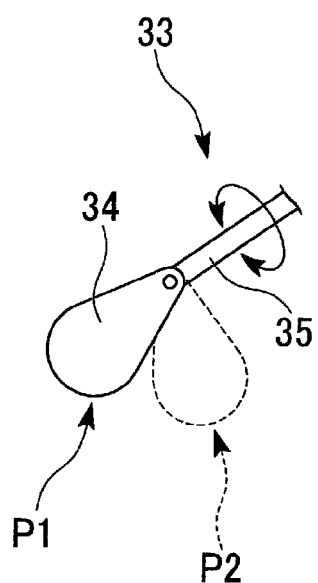
FIG. 3 is a perspective view showing a diaphragm portion of the same optical adaptor.

The diaphragm portion 33 includes: a diaphragm member 34 which has a size capable of blocking out only one of the first optical path and the second optical path; and an axial driving member 35 to which the diaphragm member 34 is attached. The driving member 35 is connected to a driving mechanism (not shown) such as a motor. As shown in FIG. 3, the optical path to be blocked out can be switched by rotating the driving member 35 around the axis thereof to move the diaphragm member 34 to the position P1 where the first optical path is blocked out or the position P2 where the second optical path is blocked out.

The optical adapter 30 further includes an illumination device (not shown) which illuminates the front view of the insertion portion 20.

The operation portion 40 includes a dial knob 41 which is used to input operations such as an operation for bending the bent portion 21. The operation portion 40 and the processing device 100 are connected to each other via a universal cable 42.

Figure 4:
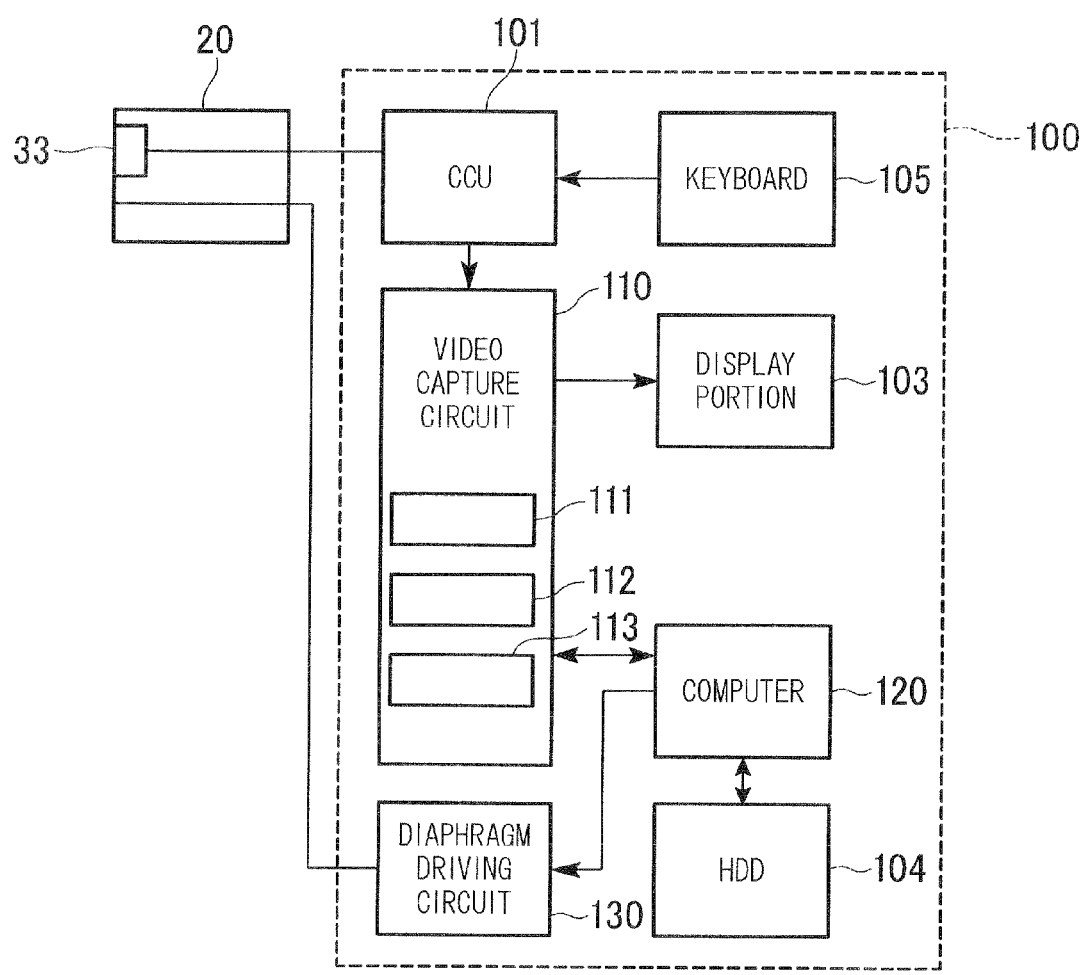
FIG. 4 is a block diagram of a processing device in the same endoscope apparatus.

FIG. 4 is a block diagram of the processing device 100. The processing device 100 includes: a camera control unit (hereinafter referred to as CCU) 101 which converts an image signal from the endoscope 10 into a video signal such as an NTSC signal; a video capture circuit 110 which converts the video signal into a digital still image signal; a computer 120 which performs various processing on the basis of the digital image signal from the video capture circuit 110; a diaphragm driving circuit 130 which drives the diaphragm portion 33 to switch the optical path to be blocked out; a display portion 103 which displays an acquired image, a processed image, and the like; a hard disk drive (hereinafter referred to as HDD) 104 which stores or plays control processing information, image information, and the like; and a keyboard 105 for input operation. A light source may be provided in the processing device 100 if the illumination device of the optical adaptor is a light guide or the like.

The video capture circuit 110 includes a first memory 111, a second memory 112, and a third memory 113. Images used to perform the stereo measurement and the like are stored in the first, second and third memories 111, 112 and 113.

Figure 5:
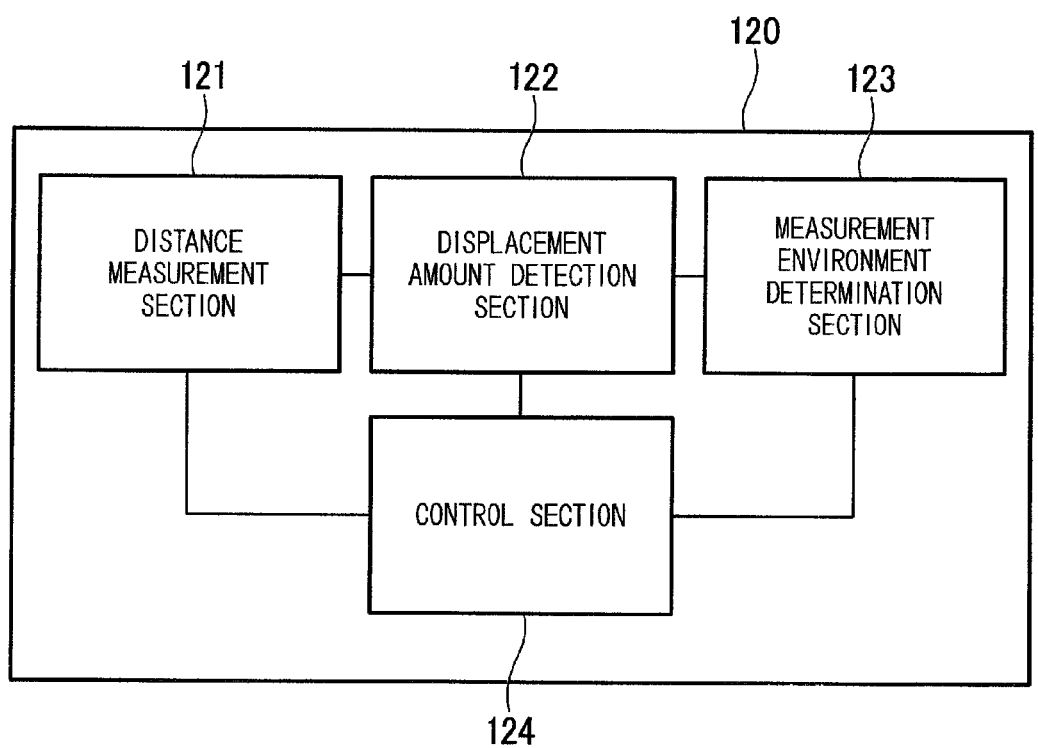
FIG. 5 is a functional block diagram of a computer of the same processing device.

FIG. 5 is a functional block diagram of the computer 120. The computer 120 includes: a distance measurement section 121 which performs stereo measurement using images stored in the video capture circuit 110; a displacement amount detection section 122 which detects a displacement amount between two images stored in the video capture circuit 110; a measurement environment determination section 123 which determines a measurement environment (described later) on the basis of the displacement amount detected by the displacement amount detection section 122; and a control section 124 which performs controls of the entirety of the endoscope apparatus.

The diaphragm driving circuit 130 is connected to the driving mechanism which drives the driving member 35 via the insertion portion 20, and generates a voltage for driving the driving member 35 on the basis of the instruction of the control section 124 to switch the optical path to be blocked out by the diaphragm portion 33.

The procedure of the endoscope apparatus 1 having the above-described structure will be described.

A user inserts the insertion portion 20 into the inside of the subject, and observes the inside of the subject, in the same manner as the use of a general endoscope apparatus. When measuring the distance between a specific portion inside the subject and the distal end of the insertion portion 20, the user operates the operation portion 40 to perform an operation input for measuring the distance.

When receiving the operation input, the diaphragm driving circuit 130 drives the diaphragm portion 33. Then, at least one still image of the subject including the specific portion is acquired via the first objective optical system 31, and at least one still image of the subject including the specific portion is acquired via the second objective optical system 32. Then, the stereo measurement is performed using the still images on the basis of a known principle.

If the subject is moving or the insertion portion 20 is moving during the acquisition of the still images, there is a possibility that the accuracy of stereo measurement may descend or the measurement may become difficult. In the endoscope apparatus 1 of the present embodiment, in parallel with the above-described stereo measurement, the measurement environment determination section 123 determines whether or not a condition (i.e., measurement environment) of the subject and the insertion portion 20 at the point in time when the still image used for the stereo measurement is acquired is suitable for performing the stereo measurement. Hereinafter, the determination flow by the measurement environment determination section 123 will be described.

Figure 6:
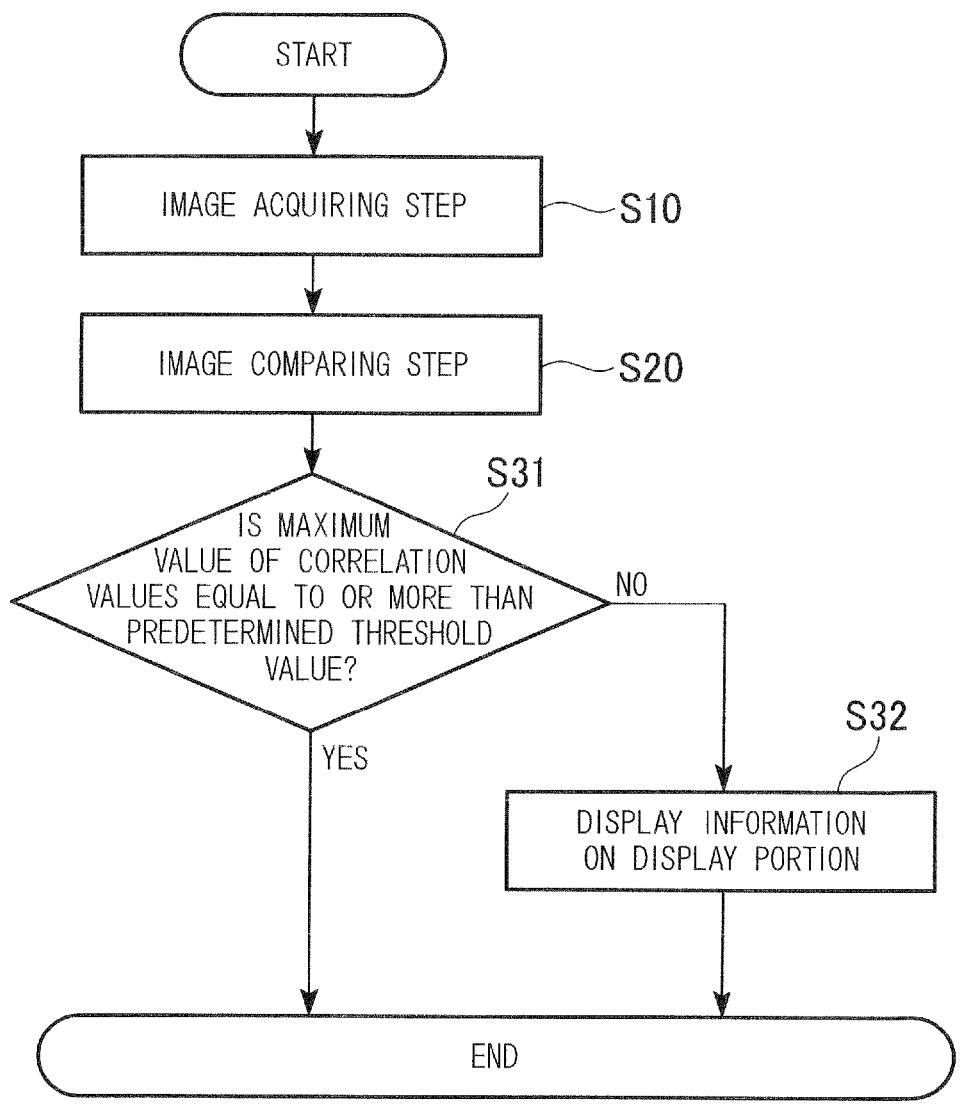
FIG. 6 is a flow chart showing a flow of a determination procedure of a measurement environment determination section in the same endoscope apparatus.

FIG. 6 shows a flow chart showing a flow of a determination procedure of the measurement environment determination section 123. First, in step S10 of an image acquiring step, another one still image in addition to the images used for the stereo measurement is acquired in order to determine the measurement environment.

Figure 7:
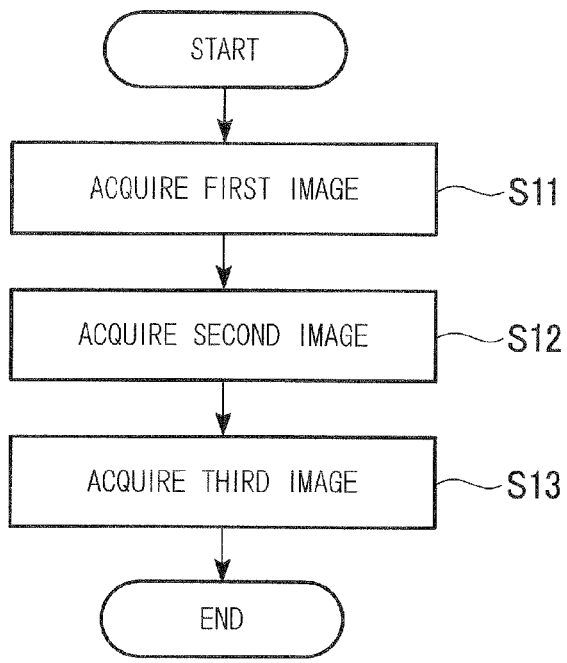
FIG. 7 is a flow chart showing details of an image acquiring step in the same determination procedure.

FIG. 7 shows a flow chart showing details of the image acquiring step S10. In step S11, a first still image (i.e., a first image) which is formed on the imaging portion 23 via the first optical path is acquired in a state where the second optical path is blocked out by the diaphragm portion 33. Subsequently, in step S12, the driving member 35 is driven to move the diaphragm portion 33 to the position where the first optical path is blocked out. Then, a second still image (i.e., a second image) which is formed on the imaging portion 23 via the second optical path is acquired. Subsequently, in step S13, the diaphragm portion 33 is returned to the position where the second optical path is blocked out, and a third still image (i.e., a third image) which is formed on the imaging portion 23 via the first optical path is acquired. The first through third still images are saved in the first through third memories 111 through 113, respectively. Note that the first through third images are acquired at the same interval of time.

In the present embodiment, the first and second images are used for the stereo measurement. Therefore, the stereo measurement using the first and second images is performed by the distance measurement section 121 in parallel with the determination by the measurement environment determination section 123.

In step S20 of an image comparing step, among the three still images acquired in the image acquiring step S10, two images acquired via the same optical path, namely the first and third images, are compared with each other.

Figure 8:
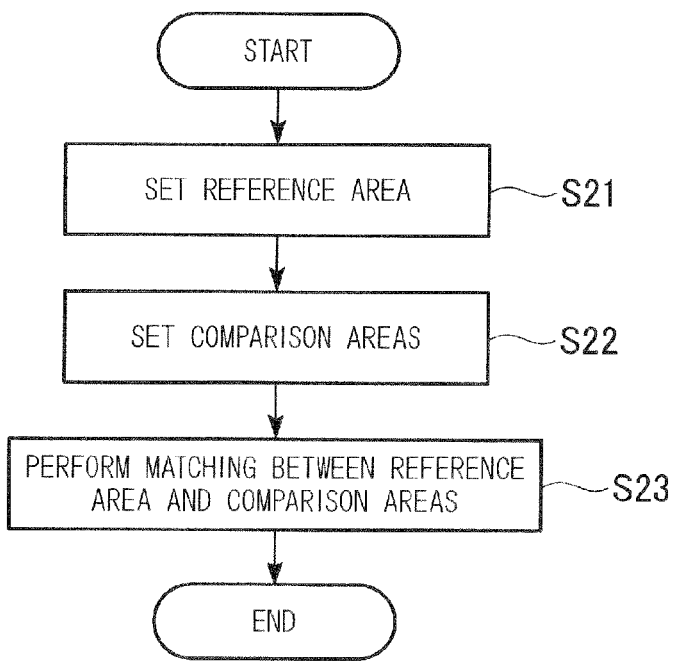
FIG. 8 is a flow chart showing details of an image comparing step in the same determination procedure.
Figure 9:
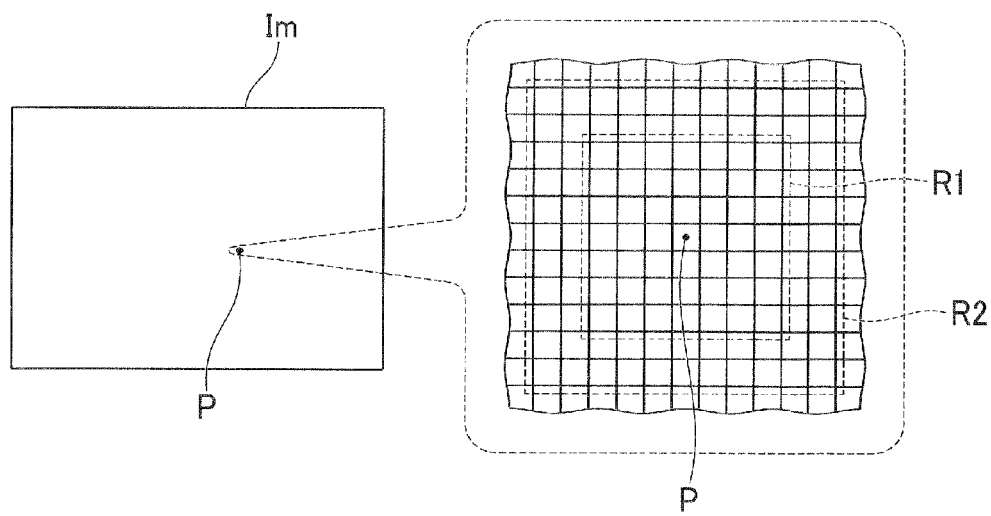
FIG. 9 is a view illustrating an attention point and a reference area in an image.

FIG. 8 shows a flow chart showing details of the image comparing step S20. In step S21, a reference area, which is a criterion for detecting a displacement amount, is set. The reference area is set in either one of the first and third images. As shown in FIG. 9, when an attention point P is specified as a pixel in an image Im, the reference area is set in a range of 3 pixels in the upper, bottom, right, and left directions from the attention point P. Therefore, the reference area is a range R1 of 49 pixels, which is 7 pixels long and 7 pixels wide, centered on the attention point P. Although the attention point P may be specified anywhere, it is preferable to specify the attention point P in the vicinity of the center of the image Im. In this case, since there is little distortion in the vicinity of the center of the image Im, it is possible to prevent the determination from being affected by the distortion.

In step S22, comparison areas are set on the other of the first and third images in which the reference area is not set. The comparison areas are 7 pixels long and 7 pixels wide, centered on 121 pixels, respectively, the 121 pixels being positioned in a range R2 of 5 pixels in the upper, bottom, right, and left directions from a pixel corresponding to the attention point P. That is, 121 comparison areas, each of which includes a range of 49 pixels, are set.

In step S23, matching between the reference area and each of the comparison areas is performed to obtain correlation values with respect to the reference area for each comparison area. The correlation values for each comparison area are stored in the displacement amount detection section 122.

In step S31, it is determined whether or not the maximum value among the obtained correlation values exceeds a predetermined threshold value (for example, 0.99). When the determination in step S31 is NO, it proves that none of the comparison areas corresponds to the reference area, that is, the displacement amount between the first and third images is 5 or more pixels. In this case, the measurement environment determination section 123 determines that an environment in the image acquiring step S10 under which images have been acquired is unsuitable for performing the stereo measurement, and the processing proceeds to step S32. On the other hand, when the determination in step S31 is YES, it is determined that the comparison area indicating the maximum value is an area corresponding to the reference area. In this case, the displacement between the first and third images is equivalent to the distance between the attention point P and the center of the comparison area indicating the maximum value. In the present embodiment, it is determined that the displacement amount is within the acceptable range from the standpoint of suitably performing the stereo measurement, and the processing terminates.

In step S32, on the basis of the determination result by the measurement environment determination section 123, information for drawing the user's attention about the distance measurement which has been performed by the user's instruction is displayed on the display portion 103. For example, a message such as "There is a problem in reliability of the measured distance" or "Perform the distance measurement once again" is displayed.

In an endoscope apparatus which can perform the stereo measurement, the accuracy of stereo measurement descends when the displacement amount between right and left image data exceeds an acceptable range due to the jiggle of a distal end of the endoscope apparatus, the movement of a subject to be measured, and the like. However, since measurement can be performed even in this case, output measurement values such as the distance are displayed on a display portion or stored in the acquired image data without any change. Therefore, there is a possibility that the user does not recognize the fact that the accuracy of stereo measurement is decreased or that images are acquired under a condition where the accuracy is decreased. In this case, the accuracy of inspection may also be decreased.

According to the endoscope apparatus 1 of the present embodiment, when the user performs the stereo measurement, the measurement environment determination section 123 determines whether or not the measurement is performed under a suitable environment in parallel with the stereo measurement. The measurement environment determination section 123 detects the displacement amount between two images, namely the first image and the third image, acquired via the same optical system at some interval of time. Further, when the displacement amount is equal to or more than a predetermined value, the measurement environment determination section 123 determines that the measurement environment is not suitable and displays information indicating that on the display portion 103. With this structure, the user can recognize the condition where there is a problem in reliability of the executed distance measurement, and the like. Therefore, the user can execute the observation while performing suitable processing, such as processing of performing the measurement again or processing of continuing the observation while checking the reliability of the data, as necessary, on the basis of the information.

In the present embodiment, the description has been made to the case in which only one attention point and only one reference area are set. However, a plurality of attention points and reference areas may be set and displacement amounts may be detected for each reference area in the same manner as is described above. In this case, a message displayed on the display portion can be changed depending on the number or the ratio of attention points where the measurement environment is determined as not suitable. Accordingly, it is possible to provide more detailed information to the user.

Further, the range of the reference area, the set range and the number of the comparison areas, and the like described above are merely one example, and they may be appropriately set depending on the required accuracy and the like.

Further, in the present invention, the description has been made to the case in which the first and third images are saved in the first memory 111 and the third memory 113, respectively. However, these images may be saved in the HDD 104 as soon as they are acquired.

Next, a second embodiment of the present invention will be described with reference made to FIGS. 10 through 12. An endoscope apparatus 51 of the present embodiment is different from the above-described endoscope apparatus 1 in that an image used for the stereo measurement is generated by correction. The components that are identical or similar to those described above will be denoted by the same reference numeral and repetitious explanations thereof will be omitted.

Figure 10:
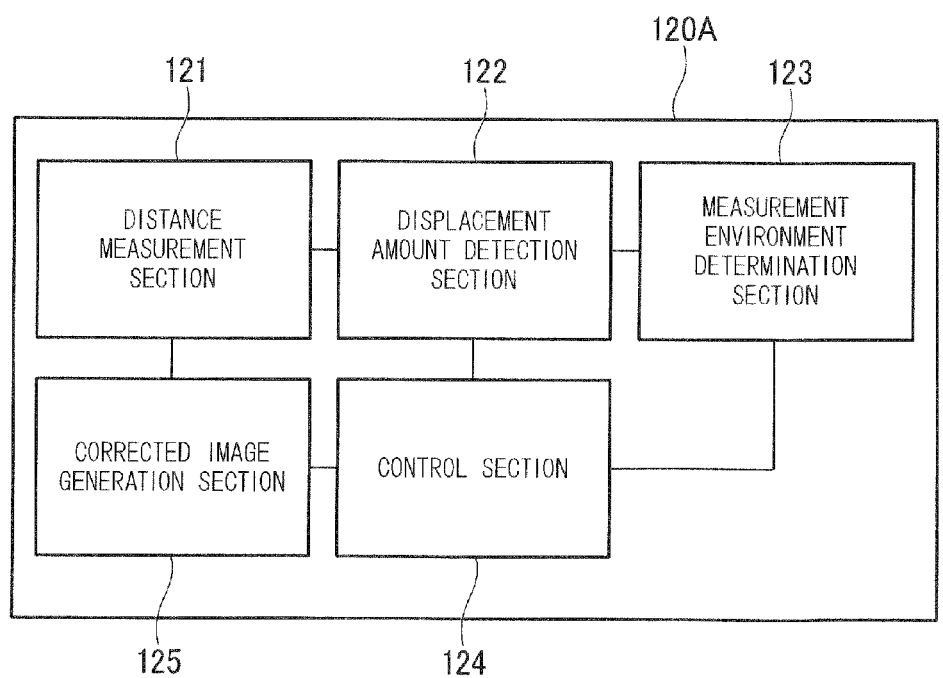
FIG. 10 is a functional block diagram of a computer in an endoscope apparatus according to a second embodiment of the present invention.

FIG. 10 is a functional block diagram of a computer 120A in the endoscope apparatus 51. The computer 120A further includes a corrected image generation section 125 which generates a corrected image on the basis of the determination result by the measurement environment determination section 123.

Figure 11:
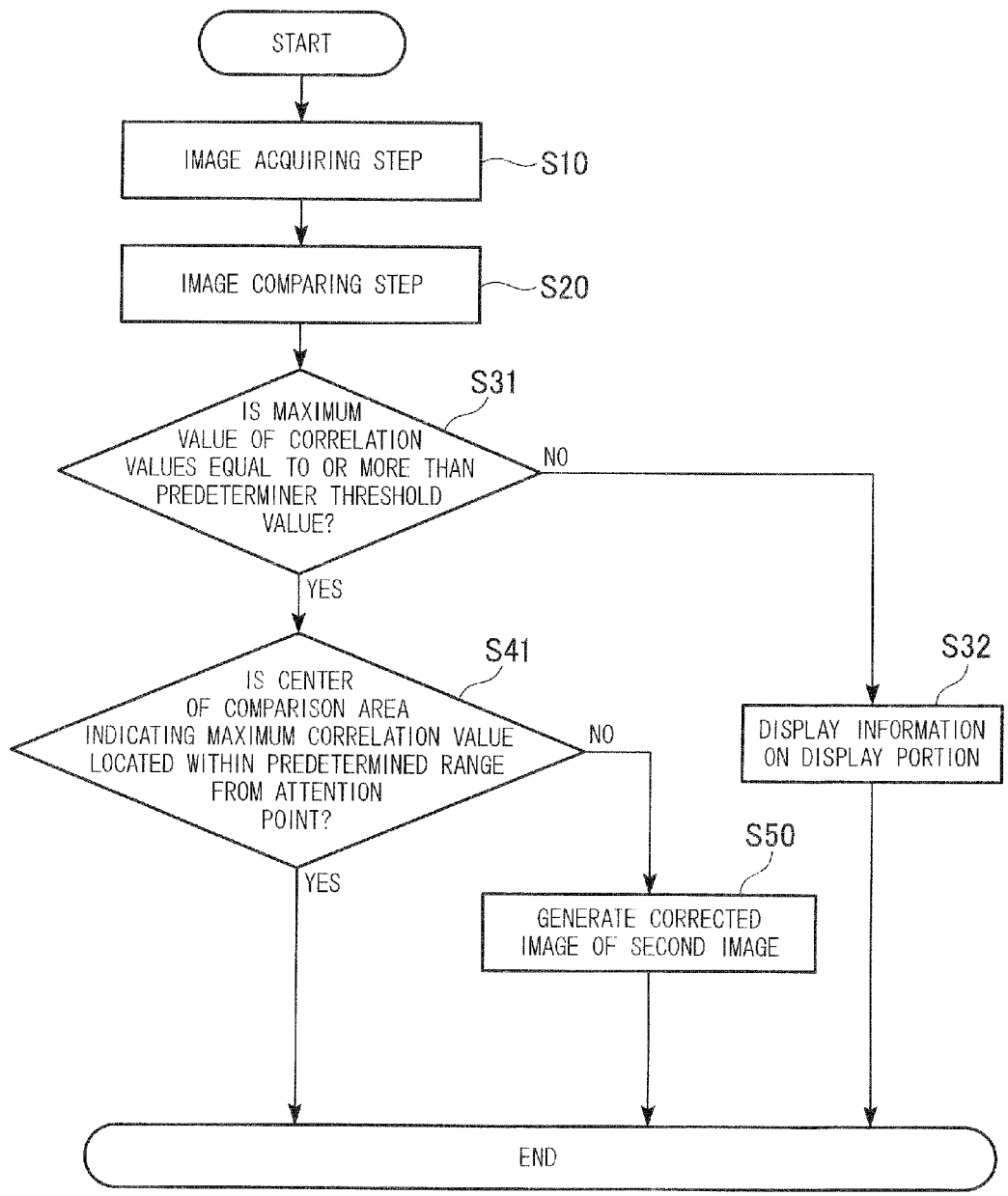
FIG. 11 is a flow chart showing a flow of a procedure of a measurement environment determination section in the same endoscope apparatus.

FIG. 11 shows a flow chart showing a flow of a determination procedure of a measurement environment determination section in the endoscope apparatus 51. In the endoscope apparatus 51, the execution of the stereo measurement is deferred until the determination by the measurement environment determination section has been completed.

As shown in FIG. 11, when the determination in step S31 is YES, the processing proceeds to step S41, and it is determined whether or not the center of the comparison area indicating the maximum correlation value is within a predetermined range from the attention point P (for example, within a range of 2 pixels in the upper, bottom, right, and left directions from the attention point P). When this determination is YES, it is determined that the displacement amount between the second image and the first and third images is within the acceptable range and there is no need to generate a corrected image, and the procedure of the measurement environment determination section 123 terminates. Then, the stereo measurement is performed by the distance measurement section 121 using the second image and one of the first and third images which is set in advance.

On the other hand, when the determination in step S41 is NO, it is determined that the displacement amount between the second image and the first and third images is out of the acceptable range. The processing proceeds to step S50, and the corrected image generation section 125 generates a corrected image of the second image in order to suitably perform the stereo measurement.

Figure 12:
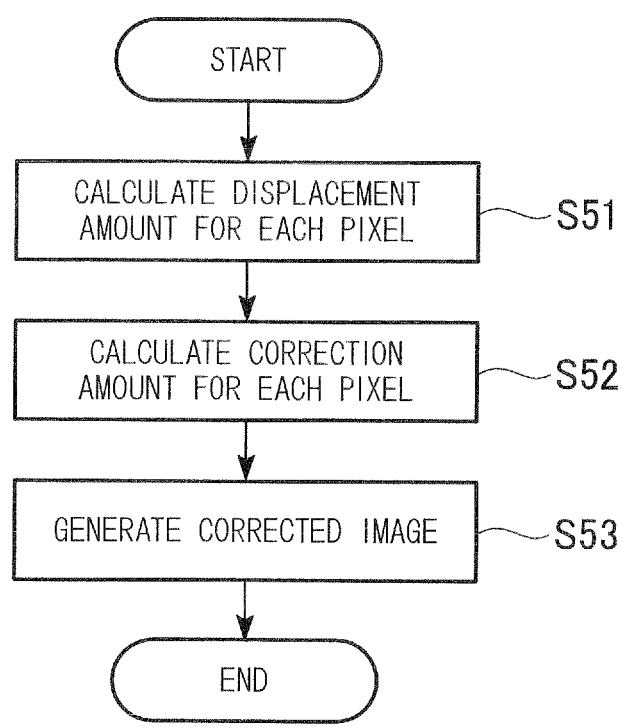
FIG. 12 is a flow chart showing a flow of generating a corrected image.

FIG. 12 shows a flow chart showing a flow of generating a corrected image of the second image.

In step S51, displacement amounts between the first and third images are identified at all of the pixels. Various methods can be used to identify the displacement amounts of the pixels. The simplest method is a method in which the displacement amount between the attention point P and the center of the comparison area indicating the maximum correlation value detected in step S23 is set as displacement amounts of all of the pixels. Alternatively, a plurality of attention points may be set to acquire information about displacement amounts thereof, and the displacement amounts of all of the pixels may be calculated by calculating the rotating center and the rotating amount of image displacement on the basis of the displacement amounts of the plurality of attention points. Alternatively, a known optical flow may be calculated on the basis of the first and third images, and the displacement amounts of all of the pixels may be calculated on the basis of the calculated optical flow.

In step S52, correction amounts for each pixel are calculated on the basis of the displacement amounts of all of the pixels acquired in step S51. In the present embodiment, since the first, second and third images are acquired at the same interval of time, if the movement of the subject and the jiggle of the insertion portion 20 are at constant speed, it is assumed that the displacement amount of the second image with respect to the first image or the third image is half of the displacement amount acquired in step S51. Therefore, in the present embodiment, the corrected image generation section 125 sets half value of the displacement amount acquired in step S51 as the displacement amount of each pixel. The set displacement amount of each pixel is stored in a correction table and saved in the HDD 104.

In step S53, the corrected image generation section 125 refers the correction table and generates a corrected image of the second image. The basic flow of generating a corrected image is as follows.

a. For a pixel (with coordinates of x1, y1) in the second image, the correction amount ($\Delta x1, \Delta y1$) of this pixel is read out from the correction table.

b. Image data of coordinates (x1+$\Delta x1$, y1+$\Delta y1$) is read out from the second image, and write this image data at the position of coordinates (x1, y1) in a corrected image to be generated.

c. This processing is subsequently performed for all of the pixels in the second image to complete the corrected image by writing image data at all of the pixels in the corrected image.

Note that the above-described procedure b is the case when a corrected image corresponding to the first image is generated. When performing the stereo measurement using the third image, it is possible to generate a corrected image corresponding to the third image by changing coordinates read out in the procedure b to (x1-$\Delta x1$, y1-$\Delta y1$).

The generated corrected image is substituted for the acquired second image, and is saved in the second memory 112. Then, the stereo measurement is performed using the first image and the second image generated by the corrected image generation section 125. At this time, a message or an icon indicating that the correction for the stereo measurement is performed may be displayed on the display portion in order to notify the user of the correction.

According to the endoscope apparatus 51 of the present embodiment, when the measurement environment determination section detects the displacement amount which is equal to or larger than a predetermined amount, a corrected image of the second image is generated by the corrected image generation section 125 and the stereo measurement is performed using the corrected image. Therefore, it is possible to suppress the descent of reliability in the stereo measurement, and it is possible to perform the observation of the subject more accurately.

In the present embodiment, the description has been made to the case in which a corrected image of the second image is generated and used for the stereo measurement together with one of the first and third images. However, a corrected image of one of the first and third images may be generated and used for the stereo measurement together with the second image.

While preferred embodiments of the invention have been described and illustrated above, it should be understood that these are exemplary of the invention and are not to be considered as limiting. Additions, omissions, substitutions, and other modifications can be made without departing from the scope of the present invention.

For example, in the above-described embodiments, the description has been made to the case in which the endoscope has two objective optical systems. However, instead of this, an endoscope in which one objective optical system is combined with a prism and the like to obtain two optical paths with parallax may be used.

Further, in the above-described embodiments, the description has been made to the case in which the first through third images are acquired at the same interval of time. However, the acquisition interval may be unequal. In this case, in the second embodiment, the correction amount of each pixel is calculated on the basis of the ratio between the acquisition interval between the first and second images, and on the basis of the acquisition interval between the second and third images.

Further, in the above-described embodiments, the description has been made to the case in which the first, second and third images are acquired in this order. However, the acquisition order of three images is not limited thereto. When three images are acquired in an order different from that in the above-described example, the acquisition interval between images may be stored, and the detection of the displacement amount, the calculation of the correction amount and the like may be performed on the basis of the stored acquisition interval.

Further, in order to display a pseudo-panorama image with wider view angle on the display portion, the endoscope apparatus may be structured such that an image acquired via the first optical path and an image acquired via the second optical path are displayed in a state where an overlapped portion of these images is superimposed and only one of these images is displayed in the overlapped portion.

The invention is not to be considered as being limited by the foregoing description, and is only limited by the scope of the appended claims.

What is claimed is:

1. An endoscope apparatus adapted to be inserted into an inside of a subject and observe the inside of the subject, the apparatus comprising:

an observation optical system which has a first optical path and a second optical path with parallax;

an imaging portion on which a light passing through the first optical path and a light passing through the second optical path are formed;

a diaphragm portion which selectively blocks out one of the first optical path and the second optical path;

a distance measurement portion which measures a distance to the subject based on parallax between a first image formed on the imaging portion via the first optical path and a second image formed on the imaging portion via the second optical path;

a displacement amount detection portion which detects a displacement amount between the first image and a third image, also formed on the imaging portion via the first optical path, acquired with a time interval therebetween; and a measurement environment determination portion which determines, based on the displacement amount, whether or not the first image and the second image are suitable for obtaining a measurement by the distance measurement portion, wherein the imaging portion acquires the first image and the third image in a state where the second optical path is blocked out by the diaphragm portion and acquires the second image in a state where the first optical path is blocked out by the diaphragm portion.

2. The endoscope apparatus according to claim 1, further comprising:

a display portion on which an image captured by the imaging portion is displayed, wherein when the measurement environment determination portion determines that the first image and the second image are not suitable for obtaining a measurement by the distance measurement portion, the measurement environment determination portion displays information announcing a determination result on the display portion.

3. The endoscope apparatus according to claim 1, further comprising:

a corrected image generation portion which generates a corrected image of at least one of the first image and the second image based on the displacement amount, when the displacement amount is equal to or more than a predetermined amount and the measurement environment determination portion determines that the first image and the second image are suitable for obtaining a measurement by the distance measurement portion.

* * * * *